(12) United States Patent
Oelund et al.

(10) Patent No.: US 7,586,019 B2
(45) Date of Patent: Sep. 8, 2009

(54) ADHESIVE PATCH

(75) Inventors: Jakob Oelund, Alleroed (DK); Carsten Sletten, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 225 days.

(21) Appl. No.: 10/550,735

(22) PCT Filed: Mar. 24, 2004

(86) PCT No.: PCT/DK2004/000203

§ 371 (c)(1),
(2), (4) Date: Sep. 26, 2005

(87) PCT Pub. No.: WO2004/087004

PCT Pub. Date: Oct. 14, 2004

(65) Prior Publication Data

US 2006/0195053 A1   Aug. 31, 2006

(30) Foreign Application Priority Data

Mar. 31, 2003   (DK) ................................ 2003 00489

(51) Int. Cl.
- *A61F 13/00*   (2006.01)
- *A61F 15/00*   (2006.01)
- *B32B 3/10*   (2006.01)
- *A61L 15/00*   (2006.01)

(52) U.S. Cl. .............................. 602/55; 602/41; 602/42; 602/43; 602/54; 602/57; 128/888; 428/131; 424/443; 424/445

(58) Field of Classification Search ............. 602/41–59; 604/332–344, 573, 304, 307, 368; 424/443–448; 128/888; 428/131

See application file for complete search history.

(56) References Cited

U.S. PATENT DOCUMENTS

| | | | |
|---|---|---|---|
| 3,802,436 A * | 4/1974 | Brondberg | 604/344 |
| 3,941,133 A | 3/1976 | Chen | |
| 4,237,889 A | 12/1980 | Gobran | |
| 4,367,732 A | 1/1983 | Poulsen et al. | |
| 4,867,748 A | 9/1989 | Samuelsen | |
| 5,051,259 A | 9/1991 | Olsen et al. | |
| 5,133,821 A | 7/1992 | Jensen | |
| 5,486,158 A * | 1/1996 | Samuelsen | 602/46 |
| 5,643,187 A | 7/1997 | Naestoft et al. | |
| 5,714,225 A * | 2/1998 | Hansen et al. | 428/114 |
| 5,716,475 A | 2/1998 | Botten et al. | |
| 5,800,415 A | 9/1998 | Olsen | |
| 5,972,452 A | 10/1999 | Takahashi et al. | |
| 6,171,594 B1 | 1/2001 | Nielsen | |

(Continued)

FOREIGN PATENT DOCUMENTS

DK   169711   7/1994

(Continued)

*Primary Examiner*—Patricia M Bianco
*Assistant Examiner*—Brandon Jackson

(57) ABSTRACT

An adhesive patch for covering a portion of the anatomical surface of a living being, said patch being able to adhere to the skin, and/or a wound on a part of the body, said patch comprising a backing layer and a layer of a skin-friendly adhesive for adhering to the skin, and said patch having a pattern of indentations wherein the indentations are in the form of a pattern of curvilinear indentations shows a flexibility capable of adapting to the contour of a skin surface or a joint that is frequently bent ensuring a snug fit and a safe grip.

19 Claims, 2 Drawing Sheets

U.S. PATENT DOCUMENTS

| | | |
|---|---|---|
| 6,303,700 B1 | 10/2001 | Chen |
| 6,420,622 B1 * | 7/2002 | Johnston et al. ............... 602/41 |
| 6,437,038 B1 | 8/2002 | Chen |
| 6,451,883 B1 | 9/2002 | Chen et al. |
| 6,652,496 B2 * | 11/2003 | Bateman .................... 604/342 |
| 6,867,342 B2 * | 3/2005 | Johnston et al. ............... 602/52 |
| 2002/0128578 A1 * | 9/2002 | Johnston et al. ............... 602/43 |

FOREIGN PATENT DOCUMENTS

| | | |
|---|---|---|
| EP | 0 256 893 A2 | 2/1988 |
| EP | 0 768 071 A1 | 4/1997 |
| EP | 0 806 210 A2 | 11/1997 |
| GB | 1 075 939 | 7/1967 |
| WO | WO 91/01118 | 2/1991 |
| WO | WO 91/01119 | 2/1991 |
| WO | WO 93/00056 | 1/1993 |
| WO | WO 93/18725 | 9/1993 |
| WO | WO 94/15562 | 7/1994 |
| WO | WO 94/18919 | 9/1994 |
| WO | WO 95/14451 | 6/1995 |
| WO | WO 99/36017 | 7/1999 |
| WO | WO 00/30576 | 6/2000 |
| WO | WO 00/54820 | 9/2000 |
| WO | WO 01/05340 A2 | 1/2001 |
| WO | WO 01/54632 A1 | 8/2001 |

* cited by examiner

ADHESIVE PATCH

This is a nationalization of PCT/DK2004/000203 filed 24 Mar. 2004 and published in English.

BACKGROUND OF THE INVENTION

1. Field of the Invention

The present invention relates to adhesive patches suitable for use for dressings, such as medical dressings for covering a portion of the anatomical surface of a living being, or, in particular, for use as adhesive barrier member for ostomy appliances, a method for preparing such adhesive patches, and methods of treating a portion of the anatomical surface of a living being, especially a protruding part of the body, and for applying an ostomy appliance comprising such adhesive patch.

In connection with surgery for a number of diseases in the gastrointestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member or base plate is attached to the wearers abdomen/back/chest. In case of a one-piece appliance, a receiving member or bag is attached to the base plate. In case of a two-piece appliance, the adhesive base plate forms part of a body side member and a receiving member or bag is attached releasably to the body side member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced.

Conventionally, dressings for the treatment or prevention of wounds or pressure sores or even unbroken skin are essentially flat dressings, which are sufficiently mouldable to be applied to flat or slightly curved areas of the body. Such flat dressings are not very suitable for applying on protruding parts of the body such as joints e.g. heels or especially elbows or knees having not only a very pronounced curvature but also being subject to constant bending which often causes wrinkling and focusing of stresses in the dressing often causing release of the adhesive and unintended detachment of the dressing.

When an ostomy appliance is placed on the abdomen of a user, the bandage has to follow the movements of the skin caused by physical activity as the user would else have a feeling of carrying a very inflexible product, or the appliance might lose its hold of the skin.

The physical activity and change of positions of the user give rise to a bending, stretching, or upsetting of the appliance. The first attack will be concentrated at the borderline between uncovered skin and skin covered by the appliance. When stretching is caused at this borderline, several events/things may happen.

If the appliance is sufficiently flexible, this effect will hardly be noticed by the user. If the flexibility of the appliance is insufficient to take up the stretching, bending and upsetting, and the adhesion to the skin is maintained, the user will notice the effect and will eventually experience a pain or itching under the appliance. If the adhesion to the skin is broken, the appliance will loosen from the skin and eventually cause a leakage.

2. Description of the Related Art

Flexibility of an ostomy appliance may be obtained in several manners. The appliance may be made very thin and having a flexible carrier sheet but a very thin layer of adhesive will due to the low mass not show a sufficient absorbing capacity to uphold an acceptable service time for the appliance. If a high absorbing capacity is desired, the thickness of the adhesive layer may be increased causing a loss of flexibility of the appliance. In this case one way to preserve the flexibility is to provide embossing or indentations in the product providing areas in which the adhesive layer is thinner. The flexibility is then obtained as the thinner areas easier yield on applied forces conserving the absorption capacity of the thicker product.

Thus, WO 93/00056 discloses that a skin-friendly dressing having grooves or ditches fully or partly surrounding a central part of the dressing has a high degree of flexibility.

EP patent No. 0 768 071 discloses a wound dressing especially for use in the sacrum area, said dressing having one or more linear depressions that assist a user in applying, flexing or folding the dressing and that the dressing may have two sets of spaced parallel depressions forming a grid which is useful in the wound assessment. The thickness of the adhesive layer at the base of the depressions should at least be as great as the thickness of the border portion of the adhesive layer.

GB patent No. 1,075,939 discloses an adhesive bandage having a thermoplastic top film provided with embossments in order to allow passage of water vapour though the film.

Published EP patent application No. 0 256 893 discloses a non-adherent dressing comprising a film which contains depressions over the wound contacting area which depressions contain a viscous pharmaceutical composition which is suitable for topical application. The depressions may be in the form of a pattern of conical depressions.

GB patent No. 1,075,939 and EP patent application No. 0 256 893 are silent with respect to flexibility.

WO 99/36017 discloses a dressing comprising a substantially water-impervious layer and a skin-friendly adhesive having a pattern of indentations, which diminishes or disappears when the dressing is moisturised. The grooves are stated to have a depth of at least 25% and more preferred at least 50% of the thickness of the dressing and it is stated that the pattern may increase the flexibility of the dressing.

The publications do not disclose the problems associated with formation of wrinkles or folds during use of a wound dressing or an ostomy appliance, which may lead to formation of canals causing risk of leaking of obnoxious smells or soiling from aggressive exudates.

Furthermore, it has been found that the flexibility of a dressing or adhesive barrier member of an ostomy appliance is important, with respect to the shape, the size and the adhesive of the dressing, not only in use but also during the application.

When applying a dressing on a joint that is frequently bent, or when applying an ostomy appliance to an uneven of folded abdomen, flexibility becomes very important as the dressing or ostomy appliance must be able to adapt to the contour of the skin surface.

SUMMARY OF THE INVENTION

The invention relates to an adhesive patch for covering a portion of the anatomical surface of a living being, said patch being able to adhere to the skin, and/or a wound on a part of the body, said patch comprising a backing layer and a layer of a skin-friendly adhesive for adhering to the skin, and said patch having a pattern of indentations.

The invention also relates to an ostomy appliance comprising an adhesive patch for covering a portion of the anatomical surface of a living being, said patch being able to adhere to the skin, and/or a wound on a part of the body, said patch comprising a backing layer and a layer of a skin-friendly adhesive for adhering to the skin, and said patch having a pattern of indentations.

Furthermore, the invention relates to a wound dressing comprising an adhesive patch for covering a portion of the anatomical surface of a living being, said patch being able to adhere to the skin, and/or a wound on a part of the body, said patch comprising a backing layer and a layer of a skin-friendly adhesive for adhering to the skin, and said patch having a pattern of indentations.

The invention also relates to a method for preparing a dressing comprising a backing layer and a layer of a skin-friendly adhesive for adhering to the skin, which dressing has a pattern of indentations.

Still further, the invention relates to a method of treating a portion of the anatomical surface of a living being, especially a protruding part of the body.

Yet further, the invention relates to a method for applying an ostomy body side member or a one-piece ostomy appliance comprising an adhesive patch for covering a portion of the anatomical surface of a living being, said patch being able to adhere to the skin, around a stoma, said patch comprising a backing layer and a layer of a skin-friendly adhesive for adhering to the skin, and said patch having a pattern of indentations.

BRIEF DESCRIPTION OF THE DRAWINGS

The invention is disclosed more in detail with reference to the drawing figures which show an embodiment of an adhesive patch of the invention.

DETAILED DESCRIPTION OF THE PRESENT INVENTION

Figure 1:
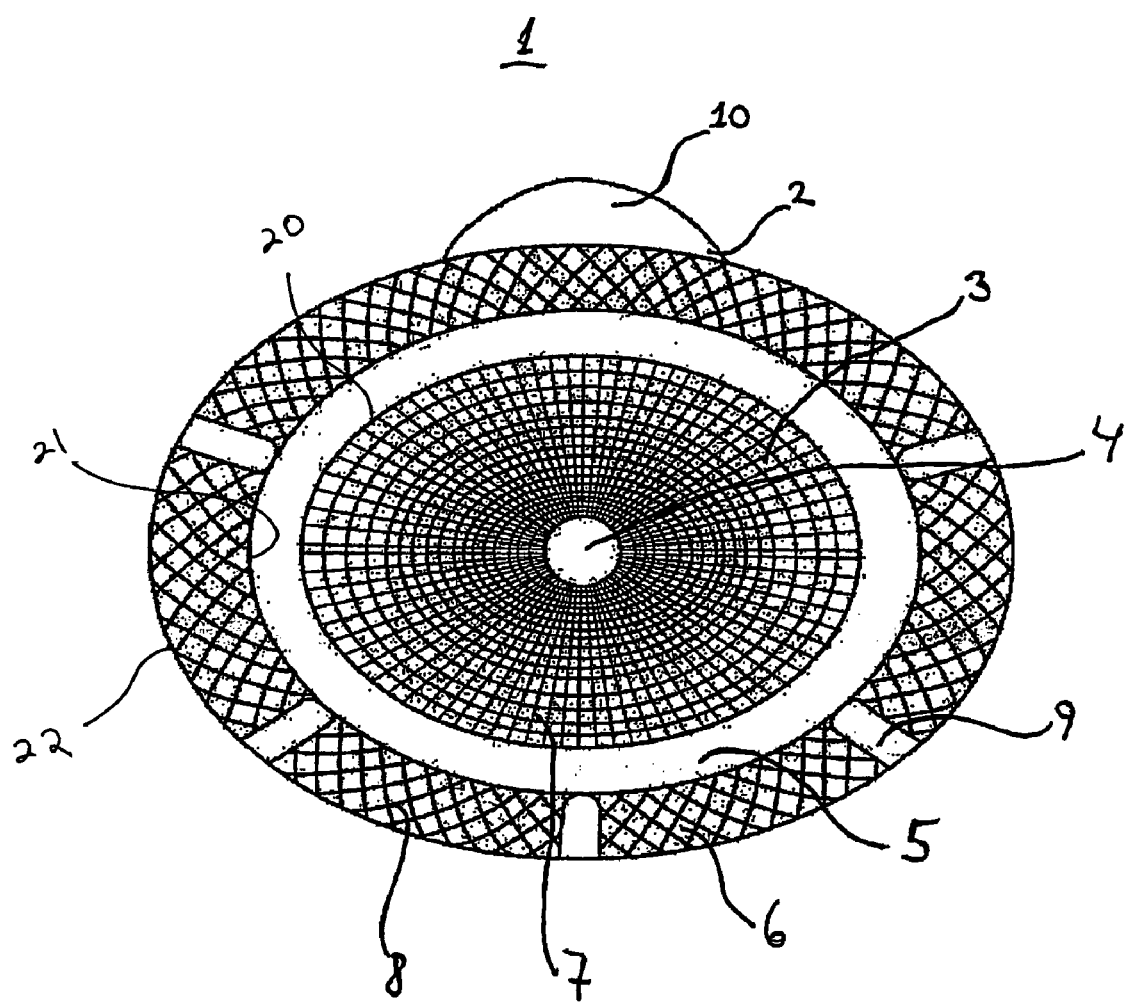
FIG. 1 shows an adhesive patch in accordance with the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to an adhesive patch for covering a portion of the anatomical surface of a living being, said patch being able to adhere to the skin, and/or a wound on a part of the body, said patch comprising a backing layer and a layer of a skin-friendly adhesive for adhering to the skin, and the patch further comprising a first central area of a relatively high thickness, a second area surrounding the first area, and a third edge area surrounding the second area, said third area has a pattern of indentations, wherein the indentations are in the form of a pattern of curvilinear indentations.

It is preferred that the indentations do not form angles with the border of the patch of 90° and 180°.

An adhesive patch comprising a network of indentations in which the lines form angles with the border of the patch of 90° and 180°, respectively, provides a flexible structure, but an attack by a force perpendicular to the border could relatively easy produce a bend perpendicular to the border, which may cause the patch to loosen. This effect is counteracted by the curvilinear indentations present in the border area of a patch of the invention wherein the indentations do not form angles with the border of the patch of 90° and 180°.

In one embodiment of the invention, the patch comprises a first central area of a relatively high thickness; a second area surrounding the first area, and a third edge area surrounding the second area wherein the first area is provided with a pattern of indentations and the third area is provided with a pattern of curvilinear indentations. In this embodiment, the second area may assist in stopping the propagation of wrinkles or folds from the edge or from a centre hole of the patch.

In another embodiment of the invention the indentations in the first area comprises a set of "radial" indentations providing flexibility perpendicular to the indentations. The term "radial" as used in the present context is intended not only to comprise directions from the centre of a circle towards the periphery but also to comprise not crossing directions from a central part of e.g. an ellipse or another closed figure towards the periphery thereof.

In a further embodiment the first area comprises set of indentations encircling the central part. Indentations of this kind are preferably present together with and crossing a set of radial indentations and provide providing a markedly increased flexibility in the central area of the patch and counteracts a stiffening or enforcing effect provided by a set of radial indentations.

In a further embodiment of the invention wherein the indentations in the third area are in the form of two or more series of curvilinear indentations crossing each other a very high degree of flexibility is obtained in the border area between free skin and neighbouring skin covered by the patch and furthermore does not provide straight lines facilitating the progressing of a wrinkle or fold. This embodiment is believed rather to deflect such progressing wrinkles or folds reducing the risk of causing a leak.

In yet a further embodiment the indentations are in the form of grooves having a level bottom. The presence of a level bottom of the indentations improves the flexibility and capacity for taking up propagating wrinkles or folds in a level where the damage caused by the wrinkles or folds is kept barely noticeable and also to be able to absorb the effect of larger folds.

It has been found suitable when the width of the indentations, is in the magnitude of from about 0.5 to about 3 millimetres, e.g. 1-2 millimetres, suitably 1.2 millimetres providing a suitable flexibility. It is suitable when the width of a level at the bottom of the indentations is of the same order of magnitude as the stated for the width above.

In order to ensure a suitable flexibility of the patch it is preferred that the indentations have depth of at least two thirds of the total thickness of the patch. In accordance with a preferred embodiment the indentations have depth of at least 75% of the total thickness of the patch, more preferred up to 90% and even exceeding 90% of the total thickness of the patch. Thus, the patch may be considered as a number of thick parts connected by thinner bridging parts. The bridging parts are preferably sufficiently large and present in a sufficient number to allow stress originated from movement to be relaxed without proceeding from one thick part to the next.

The curvilinear indentations, when the patch of the invention is seen from above, may suitably be defined by a mathematical function of second or higher order or a hyperbolic function. Such functions give rise to curvilinear patterns such as circles or super-circles, ellipses or super-ellipses, hyperboles and parables or parts thereof.

In a suitable embodiment of the invention the third area is provided with radial zones having a thickness comparable with the thickness of the material in the bottom of the indentations in the third area. Such zones are suitably without indentations. The presence of such zones at the border of the patch provides folding zones capable of absorbing a local high degree of bending caused e.g. when an ostomate is in sitting position and thus prolong the service time of the patch.

In one embodiment the invention relates to an ostomy appliance comprising an adhesive patch of the invention, said patch being able to adhere to the skin, said patch comprising a backing layer and a layer of a skin-friendly adhesive for adhering to the skin, and said patch having a pattern of indentations wherein the patch comprises a first central area of a relatively high thickness and a hole for accommodating a stoma, a second area surrounding the first area for attaching a collecting bag or a coupling device, and a third edge area surrounding the second area, wherein the first and third areas are provided with indentations and wherein the indentations in the third area are in the form of a pattern of curvilinear indentations.

An ostomy appliance according to the invention may be in the form of a body side member or in the form of a one-piece ostomy appliance comprising an adhesive patch of the invention. A body side member comprises a coupling means known per se for releasable attachment of a receiving bag.

A skin-friendly adhesive may be any skin-friendly adhesive known per se, e.g. an adhesive comprising hydrocolloids or other moisture absorbing constituents for prolonging the time of use. The adhesive may e.g. be of the type disclosed in those disclosed in U.S. Pat. No. 4,367,732, 5,051,259, 5,714, 225, 6,171,594, 6,303,700, 6,451,883, or 6,437,038, or in WO Application Nos. 00/54820, or 01/05340.

A protective cover or release liner may for instance be siliconized paper. It does not need to have the same contour as the patch, e.g. a number of patches may be attached to a larger sheet of protective cover. The protective cover is not present during the use of the patch of the invention and is therefore not an essential part of the invention.

The outer periphery of a patch of the invention is preferably bevelled in analogy with the disclosure of U.S. Pat. No. 4,867, 748 or U.S. Pat. No. 5,133,821 in order to reduce the risk of "rolling-up" the edge of the dressing reducing the wear-time. The edge is preferably bevelled so that the thickness adjacent to the edge does not exceed about 30% of the maximum thickness of the dressing; more preferred not exceeding 25% of the maximum thickness.

A coupling means may be any system known per se for attaching receiving bags to ostomy body side members and may suitably be matching coupling rings of the type disclosed in WO 93/18725, WO 94/18919, WO 91/01118, WO 91/01119 or matching flanges for adhesive connection of the type disclosed in U.S. Pat. No. 5,800,415, WO 00/30576, or WO 01/54632.

A collection bag may be made in analogy with and from materials conventionally used for the preparation of ostomy appliances. Such materials are suitably films composed of any suitable material, which is heat sealable and sufficiently impervious for unpleasant odours such as polyolefin films or combinations of such films, e.g. polyethylene or a co-extrudate of polyethylene and polyvinylidene chloride. Suitably the bag is made from front and rear walls welded in a manner known per se along the rim forming a bag. When cutting or punching the walls, an opening for receiving a stoma is suitably also punched in the wall to form the rear wall.

A collecting bag or a coupling device may be attached to the second zone using an adhesive or by welding in a manner known per se.

In another embodiment, the invention relates to a wound dressing comprising an adhesive patch of the invention, said patch being able to adhere to the skin, said patch comprising a backing layer and a layer of a skin-friendly adhesive for adhering to the skin, and said patch having a pattern of indentations wherein the patch comprises a first central area of a relatively high thickness, optionally a second area surrounding the first area, and a third edge area surrounding the first or second area, wherein the first and third areas are provided with indentations and wherein the indentations in the third area are in the form of a pattern of curvilinear indentations.

A wound dressing of the invention may in one embodiment of the invention be in the form of a mono-phase adhesive, i.e. made from one adhesive component or in accordance with another embodiment of the invention be in the form of a two-zone adhesive, e.g. of the general type disclosed in U.S. Pat. No. 5,714,225, i.e. a part of or all of the adhesive areas of the dressing being constituted by more than one type of adhesive.

The backing layer may be made from any suitable thermoplastic material known per se for use in the preparation of wound dressings or ostomy appliances e.g. foam, a non-woven layer or a polyurethane, polyethylene, polyester or polyamide suitable for attachment of a collecting bag or coupling means using an adhesive or by welding.

The backing layer of the patch may e.g. be a water impervious layer or film may be of any suitable material known per se for use in the preparation of wound dressings e.g. a foam, a non-woven layer or a polyurethane, polyethylene, polyester or polyamide film. In accordance with the invention it has been found in practice that when using a thinner backing layer or film than is normally used when preparing medical dressings, an improved stretchability and adaptability is obtained at the same time as the modulus is reduced. These properties are obtained using the same load of adhesive as is conventionally used, and thus, the conventional properties of the adhesive are retained as opposed to the case in which the load of adhesive was lowered giving a risk of insufficient absorbing capacity.

The water impervious layer or film is preferably a low-friction flexible polymer film reducing the risk of unwanted stress in an exposed area. A suitable material for use as water impervious layer is a film conventionally used as backing layer in the preparation of wound dressings, suitably having a thickness of about 30 microns.

An especially suitable material for use as a water impervious film is a polyurethane film. A preferred low friction film material is disclosed in U.S. Pat. No. 5,643,187.

A dressing of the invention may preferably be sterilised for avoiding the risk of causing infections when applied to skin areas having broken skin.

The invention also relates to a method for preparing an adhesive patch for covering a portion of the anatomical surface of a living being, said patch comprising a backing layer and a layer of a skin-friendly adhesive for adhering to the skin, and said patch having a pattern of indentations wherein the indentations are in the form of a pattern of curvilinear indentations, which method comprises providing a supply of patches comprising a backing layer and a layer of skin friendly adhesive, placing the patches in a press together with a mould having a surface corresponding to the desired pattern of indentations and providing a sufficient pressure to provide the desired pattern of indentations. The method may be carried out in a manner known per se and may be carried out in a stepwise manner or in a continuous manner as found appropriate. The materials for making a mould and the process conditions may be established by the skilled in the art by routine work considering the intended use, e.g. for covering wounds, for protection against abrasion or for ostomy appliances for use after colostomy, ileostomy, or nephrostomy or ureterostomy.

In the drawings is shown a preferred embodiment of an adhesive patch 1 for use for an ostomy appliance. The patch is able to adhere to the skin and includes a backing layer 2 and a layer of a skin-friendly adhesive for adhering to the skin. The patch has a pattern of indentations and includes a central first area 3 of a relatively high thickness and a central hole 4, a second area 5 surrounding the first area for attaching a collecting bag or a coupling device, and an edge third area 6 area surrounding the second area. As shown in FIG. 1, the first area 3 is bounded by an outer border 20 which defines the extent of the first area 3 relative to the second area 5. Similarly, the third area 6 is bounded by an inner border 21 which defines the extent of the third area 6 relative to the second area 5. The outer boundary of the third area corresponds with the rim 22 of the patch. The first and third areas are provided with indentations 7 and 8, respectively, with the indentations 8 in the third area being in the form of a pattern of curvilinear indentations. As shown, the pattern of indentations in the first area, which includes radial indentations that intersect with and cross substantially concentric indentations encircling the hole 4, is different from the pattern of curvilinear indentations in the third area. This embodiment is further provided with radial zones 9 in the third area which have a thickness comparable with the thickness of the material in the bottom of the indentations in the third area. In addition, the backing layer 2 is provided with an ear 10 protruding from the rim 22 of the patch for an easy grip.

Figure 2:
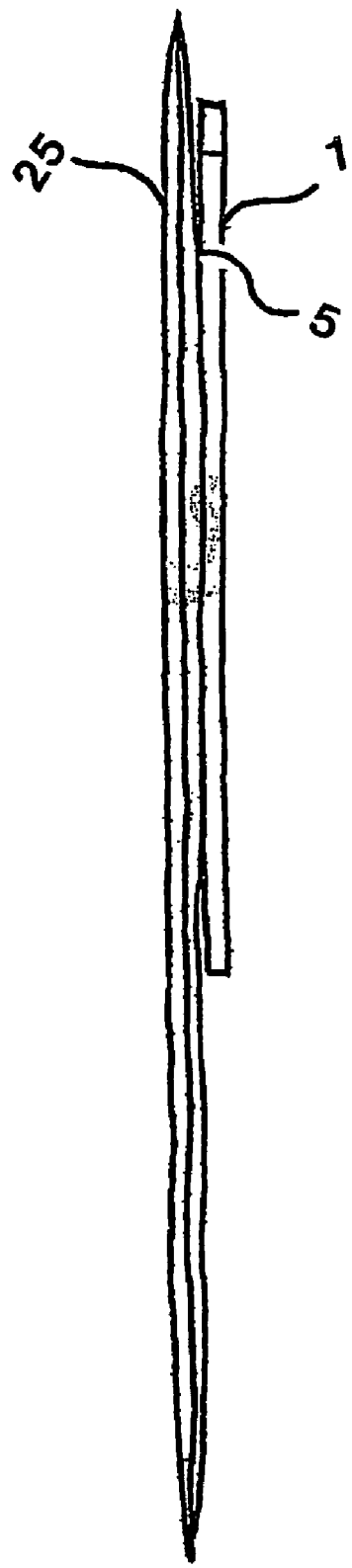
FIG. 2 shows an ostomy appliance with a collecting bag attached to the adhesive patch of FIG. 1.

FIG. 2 shows an ostomy appliance including a patch 1 with a collecting bag 25 attached thereto.

Still further, the invention relates to a method of treating a portion of the anatomical surface of a living being, especially a protruding part of the body comprising applying a dressing for covering the portion of the anatomical surface of a living being, said dressing comprising an adhesive patch for covering a portion of the anatomical surface of a living being, said patch being able to adhere to the skin, around a stoma, said patch comprising a backing layer and a layer of a skin-friendly adhesive for adhering to the skin, and said patch having a pattern of indentations wherein the indentations are in the form of a pattern of curvilinear indentations said method comprising locating the portion to be covered, adapting the curvature of the dressing for better fitting the anatomical surface to be covered, and bringing the adhesive patch to seal against the skin in the area to be covered.

Yet further, the invention relates to a method for applying an ostomy body side member or a one-piece ostomy appliance comprising an adhesive patch for covering a portion of the anatomical surface of a living being, said patch being able to adhere to the skin, around a stoma, said patch comprising a backing layer and a layer of a skin-friendly adhesive for adhering to the skin, and said patch having a pattern of indentations wherein the indentations are in the form of a pattern of curvilinear indentations and a hole for receiving a stoma, said method comprising locating the stoma, optionally adapting the size of the hole to the stoma, aligning the stoma and the hole of the adhesive patch, placing the body side member or ostomy appliance with the stoma projecting into the hole of the wafer, adapting the curvature of the patch for better fitting the anatomical surface neighbouring the stoma, and bringing the adhesive patch to seal against the abdomen of the ostomate around the stoma.

DESCRIPTION OF THE PREFERRED EMBODIMENTS

The invention is now explained more in detail with reference to the drawings showing a preferred embodiment of the invention.

In the drawings is shown a preferred embodiment of an adhesive patch 1 for use for an ostomy appliance, said patch being able to adhere to the skin, said patch comprising a backing layer 2 and a layer of a skin-friendly adhesive for adhering to the skin, and said patch having a pattern of indentations wherein the patch comprises a first central area 3 of a relatively high thickness and a central hole 4, a second area 5 surrounding the first area for attaching a collecting bag or a coupling device, and a third edge 6 area surrounding the second area, wherein the first and third areas are provided with indentations 7,8 and wherein the indentations 8 in the third area are in the form of a pattern of curvilinear indentations. This embodiment is further provided with radial zones in the third area, said zones 9 having a thickness comparable with the thickness of the material in the bottom of the indentations in the third area and the backing layer 2 is provided with an ear 10 protruding from the rim of the patch for an easy grip.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An adhesive patch for covering a portion of the anatomical surface of a living being, said patch being able to adhere to the skin, and/or a wound on a part of the body, said patch comprising a backing layer and a layer of a skin-friendly adhesive for adhering to the skin, and the patch further comprising a central first area defined by an outer border and a central hole and provided with a first set of indentations that encircle said central hole and radial indentations extending radially from the central hole, that cross said first set of indentations, a second area surrounding the first area and separated therefrom by said first area outer border, and a third area surrounding the second area, said third area bounded by a rim of said patch and an inner border to define a substantially annular area therebetween, said third area covered by a pattern of curvilinear indentations.

2. The patch as claimed in claim 1 wherein the indentations in the third area are in the form of two or more series of curvilinear indentations intersecting with and crossing each other.

3. The patch as claimed in claim 1 wherein the curvilinear indentations are in the form of grooves having a level bottom.

4. The patch as claimed in claim 1 wherein the curvilinear indentations are defined by a mathematical function of second or higher order or a hyperbolic function.

5. The patch as claimed in claim 1 wherein the third area is provided with radial zones having a thickness comparable with a thickness of the material in the bottom of the indentations in the third area.

6. The patch as claimed in claim 1 wherein said pattern of curvilinear indentations in said third area is a cross-hatched pattern.

7. The patch as claimed in claim 6 wherein said curvilinear indentations in said crosshatched pattern form angles with the patch rim that are other than 90° and 180°.

8. The patch as claimed in claim 7 wherein said curvilinear indentations in said crosshatched pattern extend to the patch rim.

9. A wound dressing comprising an adhesive patch having a backing layer and a layer of a skin-friendly adhesive for adhering to the skin, said patch having a central area and an edge area surrounding the central area and extending to a rim of said dressing, said central and edge areas having different thicknesses and being respectively provided with indentations having different patterns, with the indentations in the edge area being in the form of a pattern of curvilinear indentations that extends to an outermost edge of said rim and that meet said rim at angles of other than 90° and 180°, the thickness in said edge area being less than the thickness in said central area for greater flexibility in said edge area.

10. The wound dressing as claimed in claim 9 further comprising an intermediate area between said central and edge areas, said intermediate area having a substantially uniform thickness without indentations.

11. The wound dressing as claimed in claim 9 wherein said curvilinear indentations have a depth of at least two-thirds of a total thickness of said dressing.

12. The wound dressing as claimed in claim 9 wherein the pattern of indentations in the central area includes radial indentations that intersect with a set of indentations that encircle a central point of the dressing to form a crosshatched pattern.

13. The wound dressing as claimed in claim 12 wherein the indentations in the edge area are in the form of two or more series of curvilinear indentations intersecting with and crossing each other.

14. The adhesive patch as claimed in claim 9 wherein the central area includes a central hole and a set of substantially concentric indentations encircling the central hole.

15. The adhesive patch as claimed in claim 14 wherein the central area further includes radial indentations that intersect with and cross said concentric indentations to form a cross-hatched pattern.

16. An adhesive patch for covering a portion of the anatomical surface of a living being, said patch being able to adhere to the skin, and/or a wound on a part of the body, said patch comprising a backing layer and a layer of a skin-friendly adhesive for adhering to the skin, and the patch further comprising a central first area defined by a central hole and an outer border, a second area surrounding the first area and separated therefrom by said first area outer border, and a third area surrounding the second area, said third area bounded by a rim of said patch and an inner border to define a substantially annular area therebetween, said central first area having a pattern of indentations encircling the central hole crossed by radial indentations, said second area having a substantially uniform thickness without indentations, and said third area covered by a pattern of curvilinear indentations that includes two or more series of curvilinear indentations intersecting with and crossing each other in a cross-hatched pattern so as to form angles with the patch rim that are other than 90° and 180°.

17. The patch as claimed in claim 16 wherein a thickness of said patch in said central first area is greater than in said third area.

18. The patch as claimed in claim 16 wherein said indentations are in the form of grooves having a level bottom to improve flexibility and capacity for taking up wrinkles or folds.

19. The patch as claimed in claim 16 wherein the third area is provided with radial ungrooved zones having a thickness comparable with a thickness of the patch in bottoms of the indentations in the third area.

\* \* \* \* \*